United States Patent
Hou et al.

(10) Patent No.: US 12,257,279 B1
(45) Date of Patent: Mar. 25, 2025

(54) TRADITIONAL CHINESE HERBAL COMPOSITION FOR TREATMENT OF BACTERIAL VAGINOSIS AND PREPARATION METHOD THEREOF

(71) Applicant: The third people's hospital of chengdu, Chengdu (CN)

(72) Inventors: Jun Hou, Chengdu (CN); Xudong Wen, Chengdu (CN); Tian Yue, Chengdu (CN); Yuan Yuan, Chengdu (CN); Xiao Liu, Chengdu (CN); Jiali Yang, Chengdu (CN); Jian He, Chengdu (CN); Yue Tang, Chengdu (CN)

(73) Assignee: The third people's hospital of chengdu, Chengdu (CN)

( * ) Notice: Subject to any disclaimer, the term of this patent is extended or adjusted under 35 U.S.C. 154(b) by 0 days.

(21) Appl. No.: 18/972,246

(22) Filed: Dec. 6, 2024

Related U.S. Application Data

(63) Continuation of application No. PCT/CN2024/084662, filed on Mar. 29, 2024.

(30) Foreign Application Priority Data

Apr. 7, 2023 (CN) .......................... 202310365836.0

(51) Int. Cl.
| | | |
|---|---|---|
| *A61K 36/282* | (2006.01) | |
| *A61K 35/00* | (2006.01) | |
| *A61K 35/747* | (2015.01) | |
| *A61K 36/185* | (2006.01) | |
| *A61K 36/284* | (2006.01) | |
| *A61K 36/288* | (2006.01) | |
| *A61K 36/344* | (2006.01) | |
| *A61K 36/355* | (2006.01) | |
| *A61K 36/46* | (2006.01) | |
| *A61K 36/489* | (2006.01) | |
| *A61K 36/54* | (2006.01) | |
| *A61K 36/704* | (2006.01) | |
| *A61K 36/71* | (2006.01) | |
| *A61K 36/718* | (2006.01) | |
| *A61K 36/79* | (2006.01) | |
| *A61K 36/9068* | (2006.01) | |
| *A61P 15/02* | (2006.01) | |

(52) U.S. Cl.
CPC .......... *A61K 36/282* (2013.01); *A61K 35/747* (2013.01); *A61K 36/185* (2013.01); *A61K 36/284* (2013.01); *A61K 36/288* (2013.01); *A61K 36/344* (2013.01); *A61K 36/355* (2013.01); *A61K 36/46* (2013.01); *A61K 36/489* (2013.01); *A61K 36/54* (2013.01); *A61K 36/704* (2013.01); *A61K 36/71* (2013.01); *A61K 36/718* (2013.01); *A61K 36/79* (2013.01); *A61K 36/9068* (2013.01); *A61P 15/02* (2018.01); *A61K 2035/115* (2013.01); *A61K 2236/19* (2013.01); *A61K 2236/331* (2013.01)

(58) Field of Classification Search
CPC .. A61K 36/282; A61K 35/747; A61K 36/185; A61K 36/284; A61K 36/288; A61K 36/344; A61K 36/54; A61K 36/718; A61K 36/79; A61K 36/9068; A61K 2236/19; A61K 2236/331
See application file for complete search history.

(56) References Cited

FOREIGN PATENT DOCUMENTS

| | | | |
|---|---|---|---|
| CN | 102743719 A | | 10/2012 |
| CN | 104225015 A | * | 12/2014 |
| CN | 105031077 A | | 11/2015 |
| CN | 108272915 A | | 7/2018 |
| CN | 116350739 A | | 6/2023 |

* cited by examiner

*Primary Examiner* — J. E. Angell
*Assistant Examiner* — Jacob A Boeckelman
(74) *Attorney, Agent, or Firm* — Nitin Kaushik

(57) ABSTRACT

The present disclosure relates to the technical field of traditional Chinese herbal composition, and in particular to a traditional Chinese herbal composition for the treatment of bacterial vaginosis and a preparation method thereof. The traditional Chinese herbal composition for the treatment of bacterial vaginosis provided by the present disclosure is prepared from the following components in parts by weight: 40-50 parts of Zingiberis Rhizoma Recens, 35-45 parts of Schisandrae *Chinensis* Fructus, 30-40 parts of *Cinnamomi* Cortex, 30-40 parts of Artemisiae *Argyi* Folium, 25-35 parts of Codonopsis Radix, 25-35 parts of a compound traditional Chinese herbal fermentation broth, 20-30 parts of Pulsatillae Radix, 20-25 parts of Lonicerae Japonicae Flos, 15-20 parts of *Taraxaci* Herba, 15-20 parts of Akebiae Caulis, 10-15 parts of Polygoni Cuspidati Rhizoma et Radix, and 5-10 parts of Atractylodis Macrocephalae Rhizoma.

10 Claims, No Drawings

TRADITIONAL CHINESE HERBAL COMPOSITION FOR TREATMENT OF BACTERIAL VAGINOSIS AND PREPARATION METHOD THEREOF

CROSS-REFERENCE TO RELATED APPLICATIONS

The application claims priority to Chinese patent application No. 2023103658360, filed on Apr. 7, 2023, the entire contents of which are incorporated herein by reference.

TECHNICAL FIELD

The present disclosure relates to the technical field of traditional Chinese herbal composition, and in particular to a traditional Chinese herbal composition for the treatment of bacterial vaginosis and a preparation method thereof.

BACKGROUND

Normally, the vagina itself has a self-cleansing action, which is due to a large amount of lactobacilli in the vagina. Not only can the lactobacilli maintain the normal pH in the vagina, but also they can prevent the invasion of foreign microorganisms. However, once such an acid-base balance in the human body is disrupted, lactobacilli will decrease, and other anaerobes such as *Mobiluncus* sp., *Gardnerella* sp., *Mobiluncus* sp., *Bacteroides* sp., *Peptostreptococcus* sp., and *Potphyromnas* sp. will multiply, leading to bacterial vaginosis (BV). Bacterial vaginosis is a mixed infection of *Gardnerella vaginalis* and some anaerobes, which leads to imbalanced microecology in the vagina, increased vaginal secretions, leucorrhea with a fishy smell, and vulvar pruritus and burning. Bacterial vaginosis can be divided into *Haemophilus* vaginitis, *Corynebacterium* vaginitis, anaerobic vaginitis, *Gardnerella* vaginitis, etc. Bacterial vaginosis can cause infertility, affect fetal development, induce other diseases (genital infection, pelvic inflammatory disease, perinephritis, painful sexual intercourse, etc.) and other adverse effects, and have an effect on the quality of life of couples. In the clinical treatment of vaginitis, medication generally includes oral chemicals, lotions, and traditional Chinese medicine (TCM) decoctions. However, due to the emergence of new pathogenic microorganisms and drug resistance, the recurrence rate of vaginitis becomes higher and the patient compliance is poor. Pharmaceuticals are effective but easy to produce drug resistance and may lead to recurrence. TCM decoctions have a bitter taste and are administered at high doses. The decoction is prone to mildew after letting stand for a long time and inconvenient to carry, with poor patient compliance. Traditional Chinese herbal gynecological lotions generally have strong anti-inflammatory and trichomonacidal effects, which can effectively treat female reproductive tract infections, with broad application value and market prospects. However, there is still a lack of a TCM formula for the treatment of bacterial vaginosis with better therapeutic effect.

SUMMARY

To overcome the foregoing defects in the prior art, the present disclosure provides a traditional Chinese herbal composition for the treatment of bacterial vaginosis and a preparation method thereof.

To achieve the above objective, the present disclosure provides the following technical solutions:

The present disclosure provides a traditional Chinese herbal composition for the treatment of bacterial vaginosis, including the following components in parts by weight: 40-50 parts of Zingiberis Rhizoma Recens, 35-45 parts of Schisandrae *Chinensis* Fructus, 30-40 parts of *Cinnamomi* Cortex, 30-40 parts of Artemisiae *Argyi* Folium, 25-35 parts of Codonopsis Radix, 25-35 parts of a compound traditional Chinese herbal fermentation broth, 20-30 parts of Pulsatillae Radix, 20-25 parts of Lonicerae Japonicae Flos, 15-20 parts of *Taraxaci* Herba, 15-20 parts of Akebiae Caulis, 10-15 parts of Polygoni Cuspidati Rhizoma et Radix, and 5-10 parts of Atractylodis Macrocephalae Rhizoma. The compound traditional Chinese herbal fermentation broth is obtained by fermenting Sophorae Flavescentis Radix, Artemisiae Annuae Herba, Eucommiae Cortex, and Coptidis Rhizoma with *Lactobacillus acidophilus*.

Preferably, the compound traditional Chinese herbal fermentation broth may be specifically prepared by the following steps:

step 1, mixing the Sophorae Flavescentis Radix, the Artemisiae Annuae Herba, the Eucommiae Cortex, and the Coptidis Rhizoma, pulverizing and sieving to collect a sieved component;

step 2, mixing the sieved component with water and conducting a first decoction to obtain a decoction A and a decoction dreg A;

step 3, mixing the decoction dreg A with the water and conducting a second decoction to obtain a decoction B and a decoction dreg B;

step 4, mixing the decoction dreg B with the water and conducting a third decoction to obtain a decoction C and a decoction dreg C;

step 5, mixing the decoctions A, B and C, and conducting vacuum concentration to $\frac{1}{6}$ to $\frac{1}{4}$ of an original volume to obtain a compound traditional Chinese herbal decoction; and step 6, inoculating the *Lactobacillus acidophilus* into the compound traditional Chinese herbal decoction for a fermentation to obtain the compound traditional Chinese herbal fermentation broth.

Preferably, in step 1, the Sophorae Flavescentis Radix, the Artemisiae Annuae Herba, the Eucommiae Cortex, and the Coptidis Rhizoma may be mixed in a mass ratio of (2-4):(1-3):(1-3):(1-2), and a mesh number for the pulverizing and sieving may be 150-250 mesh.

Preferably, in step 2, the sieved component may be mixed with the water in a ratio of 1 g:(7-9) mL; the first decoction may be conducted at a temperature of 90-100° C. for 45-55 min;

in step 3, the decoction dreg A may be mixed with the water in a ratio of 1 g:(4-6) mL; the second decoction may be conducted at a temperature of 80-90° C. for 40-50 min; and in step 4, the decoction dreg B may be mixed with the water in a ratio of 1 g:(2-4) mL; the third decoction may be conducted at a temperature of 70-80° C. for 30-40 min.

Preferably, in step 5, the vacuum concentration may be conducted at a temperature of 35-45° C.

Preferably, in step 6, an inoculum size of the *Lactobacillus acidophilus* may account for 4-6% of a volume of the compound traditional Chinese herbal decoction, and the fermentation may be conducted at a temperature of 35-40° C. for 25-45 h.

The present disclosure further provides a preparation method of the foregoing traditional Chinese herbal composition for the treatment of bacterial vaginosis, including the following steps:

step (1), mixing the Zingiberis Rhizoma Recens with the Schisandrae *Chinensis* Fructus, the *Cinnamomi* Cortex, the Artemisiae *Argyi* Folium, the Codonopsis Radix, the Pulsatillae Radix, the Lonicerae Japonicae Flos, the *Taraxaci* Herba, the Akebiae Caulis, the Polygoni Cuspidati Rhizoma et Radix and the Atractylodis Macrocephalae Rhizoma, pulverizing and sieving to collect a sieved component;

step (2), mixing the sieved component with the water for decoction to obtain a mixture; and step (3), conducting the vacuum concentration on the mixture to 1/6 to 1/4 of the original volume, and mixing the compound traditional Chinese herbal fermentation broth to obtain the traditional Chinese herbal composition for the treatment of bacterial vaginosis.

Preferably, in step 1, a mesh number for the pulverizing and sieving may be 150-250 mesh.

Preferably, in step (2), the sieved component may be mixed with the water in a ratio of 1 g:(4-6) mL, and the decoction may be conducted at a temperature of 80-90° C. for 40-50 min.

Preferably, in step (3), the vacuum concentration may be conducted at a temperature of 35-45° C.

Zingiberis Rhizoma Recens, warm in nature and pungent in taste, belongs to the lung, spleen, and stomach meridians. It has antanacathartic, expectorant and antitussive actions, and resolves poisoning from fish and crabs. It contains active pharmaceutical ingredients (APIs) such as volatile oils, gingerols, and diarylheptanoids. Volatile oils: the main components include monoterpenoids, such as α-pinene, β-pyrans and α-glutamine, with 50-60% of sesquiterpenes, 17% of oxidized sesquiterpenes, the rest being mainly monoterpenes and oxidized monoterpenes. Ginger constituent mixture is divided into gingerols, shogaols, zingerones, zingerones and gingerdiols. They all contain 3-methoxy-4-hydroxybenzene functional groups. Of them, the content of 6-gingerol is more than 30%. It has antioxidant, antibacterial, anti-inflammatory, cholesterol-lowering, antiatherosclerotic, immunopotentiating, anti-radiation, liver-protecting and anti-allergic activity. Recens contains a plurality of APIs, including ginger essential oil (0.15-0.17%), polysaccharides (5.97%), olefins (61.41%), and flavonoids (2.63%), and has a plurality of pharmacological actions, such as appetizing, spleen-fortifying, antioxidant, antitumor, cooling, anti-sunstroke, bactericidal and detoxicating actions.

Schisandrae *Chinensis* Fructus, sour and sweet in taste and warm in nature, is indicated for the treatment of enduring cough, vacuity panting, spermatorrhea, seminal efflux, frequent urination, enduring diarrhea, spontaneous sweating, night sweats, body fluid deficiency, thirst, internal heat dispersion-thirst, palpitations, and insomnia. Schisandrae *Chinensis* Fructus with excellent antibacterial activity can inhibit the growth and multiplication of common bacteria such as *Staphylococcus aureus, Klebsiella pneumoniae, Salmonella enterica*, and *Pseudomonas aeruginosa*.

*Cinnamomi* Cortex, acrid and sweet in taste and extremely hot in nature, is indicated for the treatment of sexual importance, uterine cold, cold pain in the lumbus and knees, kidney vacuity panting, upfloating of vacuous yang, vrtigo, red eyes, cold pain in the heart and abdomen, vacuity cold vomiting and diarrhea, cold hernia, abdominal pain, dysmenorrhea, and amenorrhea. *Cinnamomi* Cortex has antifungal and antibacterial activity. It has inhibitory effects on *Escherichia coli, Salmonella* sp., *Pseudomonas* sp. and multidrug-resistant bacteria.

Artemisiae *Argyi* Folium, warm in nature and bitter in taste, belongs to the liver, spleen and kidney meridians. It has actions of dispelling dampness and relieving itching when used topically. It is indicated for the treatment of hematemesis, metrorrhagia, menorrhagia, fetal bleeding, cold pain in the abdomen, irregular menstruation, uterine cold, and itchy skin. Studies have shown that Artemisiae *Argyi* Folium has antiviral, antibacterial, anti-asthmatic, expectorant, antitussive, sedative, choleretic, hemostatic, and uterine stimulant activity. Volatile oil, water extract, alcohol extract and fumigant of Artemisiae *Argyi* Folium can inhibit or kill various bacteria, fungi, viruses, and mycoplasmas.

Codonopsis Radix is sweet in taste and neutral in nature. It has actions of tonifying middle-jiao and qi, quenching thirst, fortifying the spleen and lungs, nourishing the blood and engendering the fluids. It is indicated for the treatment of spleen-lung qi vacuity, poor appetite, fatigue, cough, vacuity panting, insufficiency of qi and blood, withered-yellow complexion, palpitations, shortness of breath, thirst caused by body fluid deficiency, internal heat dispersion-thirst, laziness to speak and shortness of breath, myasthenia of limbs, poor appetite, deficiency of qi, dual vacuity of qi and liquid, dual depletion of qi and blood, and chloranemia.

Pulsatillae Radix is bitter in taste and cold in nature. It has actions of clearing heat and detoxication, and cooling the blood and checking dysentery, and is commonly indicated for the treatment of blood dysentery caused by heat toxin, pruritus vulvae, and vaginal discharges.

Lonicerae Japonicae Flos is sweet in taste and cold in nature. It has actions of clearing heat, detoxication, anti-inflammation and detumescence. It is indicated for the treatment of externally contracted wind-heat or febrile disease, heat stroke, blood dysentery caused by heat toxin, swollen welling-abscess and clove sores, pharyngitis, and a plurality of infectious diseases.

*Taraxaci* Herba is bitter and sweet in taste and cold in nature. It is mainly indicated for the treatment of swollen welling-abscess and clove sores, mammary welling-abscesses, scrofuloses, red eyes, sore throat, pulmonary welling-abscesses, intestinal welling-abscesses, damp-heat jaundice, and heat strangury with difficult painful urination.

Akebiae Caulis is bitter in taste and cold in nature. It has actions of disinhibiting urine and freeing strangury, eliminating heart vexation, inducing menstruation, and promoting lactation. It is indicated for the treatment of strangury patterns, edema, vexation, reddish urine, mouth and tongue sores, amenorrhea, scant breast milk, and damp-heat impediment.

Polygoni Cuspidati Rhizoma et Radix is slightly bitter in taste and slightly cold in nature. It has actions of disinhibiting dampness, abating jaundice, clearing heat, detoxicating, dissipating stasis, relieving pain, suppressing cough and transforming phlegm. It is indicated for the treatment of damp-heat jaundice, turbid strangury, vaginal discharges, wind-damp impediment pain, swelling and toxins of welling-abscesses and sores, burns and scalds, amenorrhea, abdominal masses, wounds due to knocks and falls, and lung-heat cough.

Atractylodis Macrocephalae Rhizoma is bitter and sweet in taste and warm in nature. It has actions of tonifying qi to invigorate spleen, drying dampness for diuresis, check sweating, and quieting the fetus. It is mainly indicated for the treatment of spleen qi vacuity, fatigued spirit, weakness, reduced eating, abdominal distention, thin sloppy stool, water-rheum collecting internally, inhibited urination, edema, phlegm-rheum dizziness, soreness due to damp impediment, spontaneous sweating due to qi vacuity, and fetal irritability.

Compared with the prior art, the present disclosure has the following beneficial effects:

1. The compound traditional Chinese herbal fermentation broth provided by the present disclosure is obtained by fermenting Sophorae Flavescentis Radix, Artemisiae Annuae Herba, Eucommiae Cortex, and Coptidis Rhizoma with *Lactobacillus acidophilus*. *Lactobacillus acidophilus* is an important member of the lactic acid bacteria family. This strain is very important for women because one of its biological products is lactic acid, which helps to maintain vaginal health. Sophorae Flavescentis Radix has heat-clearing, dampness-drying, trichomonacidal and diuretic activity. It is indicated for the treatment of heat dysentery, bloody stool, jaundice, anuresis, red and white vaginal discharges, genital swelling and itching, eczema, itchy skin, scabies, leprosy, and trichomonas vaginitis for topical use. Artemisiae Annuae Herba has actions of clearing vacuity heat, eliminating steaming bones, resolving summer heat, interrupting malaria, and abating jaundice. It is commonly indicated for the treatment of warm evil damaging yin, night fever abating at dawn, fever due to deficiency of yin, steaming bone with taxation heat, fever due to summerheat evil, malarial heat and cold, and damp-heat jaundice. The flavonoids and chlorogenic acid contained in Eucommiae Cortex can strengthen the differentiation of immune cells, improve the activity and response of immune cells, activate the immune system and enhance the development of immune organs. Chlorogenic acid can further inhibit the multiplication of pernicious bacteria and improve the microenvironment of flora. Coptidis Rhizoma has actions of clearing heat, drying dampness, draining fire and resolving toxins. It was unexpectedly found from the study of the present disclosure that the combination of Sophorae Flavescentis Radix, Artemisiae Annuae Herba, Eucommiae Cortex and Coptidis Rhizoma could significantly inhibit *Gardnerella vaginalis* (GV), *Peptostreptococcus* sp. and *Bacteroides vulgatus*. The present disclosure combines the functions of *Lactobacillus acidophilus* with the foregoing four Chinese medicinal materials by means of fermentation, and finds that they have a two-way synergistic effect. In one aspect, *Lactobacillus acidophilus* can increase the content of flavonoids, terpenoids, amino acids and other APIs in Sophorae Flavescentis Radix, Artemisiae Annuae Herba, Eucommiae Cortex and Coptidis Rhizoma, promote the conversion of non-APIs into antibacterial substances, assist in the antibacterial function thereof, improve the bioavailability thereof, and substantially enhance the antibacterial function thereof. In another aspect, the combination of Sophorae Flavescentis Radix, Artemisiae Annuae Herba, Eucommiae Cortex and Coptidis Rhizoma can further synergistically regulate the activity of fermentation strains, provide nutrients for *Lactobacillus acidophilus*, significantly promote the multiplication thereof, and colonize *Lactobacillus acidophilus* into the vagina, thus playing a role in balancing the vaginal microbiota and fundamentally solving the problem of bacterial vaginosis.

2. In the present disclosure, compounding Zingiberis Rhizoma Recens with components such as Schisandrae *Chinensis* Fructus, *Cinnamomi* Cortex, and Artemisiae *Argyi* Folium in a reasonable proportion to prepare a decoction complies with the principle of compatibility of TCM. Then, mixing with the compound traditional Chinese herbal fermentation broth not only enhances the inhibitory effect on pernicious bacteria in the vagina, making the antibacterial activity stable and long-lasting, but also supplements the number of beneficial bacteria in the vagina and improves the vaginal microbiota. Moreover, as all components are natural plant pharmaceuticals, they are safe and reliable with a warm-cold balance, and topical application thereof is gentle and non-irritating to the skin and has a significant positive effect on the treatment of bacterial vaginosis, with a very broad application prospect.

DETAILED DESCRIPTION OF THE EMBODIMENTS

The present disclosure provides a traditional Chinese herbal composition for the treatment of bacterial vaginosis, including the following components in parts by weight: 40-50 parts of Zingiberis Rhizoma Recens, 35-45 parts of Schisandrae *Chinensis* Fructus, 30-40 parts of *Cinnamomi* Cortex, 30-40 parts of Artemisiae *Argyi* Folium, 25-35 parts of Codonopsis Radix, 25-35 parts of a compound traditional Chinese herbal fermentation broth, 20-30 parts of Pulsatillae Radix, 20-25 parts of Lonicerae Japonicae Flos, 15-20 parts of *Taraxaci* Herba, 15-20 parts of Akebiae Caulis, 10-15 parts of Polygoni Cuspidati Rhizoma et Radix, and 5-10 parts of Atractylodis Macrocephalae Rhizoma. The compound traditional Chinese herbal fermentation broth is obtained by fermenting Sophorae Flavescentis Radix, Artemisiae Annuae Herba, Eucommiae Cortex, and Coptidis Rhizoma with *Lactobacillus acidophilus*.

In the present disclosure, the traditional Chinese herbal composition for the treatment of bacterial vaginosis may preferably be prepared from the following components in parts by weight: 42-48 parts of the Zingiberis Rhizoma Recens, 38-42 parts of the Schisandrae *Chinensis* Fructus, 32-38 parts of the *Cinnamomi* Cortex, 32-38 parts of the Artemisiae *Argyi* Folium, 28-32 parts of the Codonopsis Radix, 28-32 parts of the compound traditional Chinese herbal fermentation broth, 22-28 parts of the Pulsatillae Radix, 22-24 parts of the Lonicerae Japonicae Flos, 17-19 parts of the *Taraxaci* Herba, 17-19 parts by weight of Akebiae Caulis, 12-14 parts of the Polygoni Cuspidati Rhizoma et Radix, and 7-9 parts of the Atractylodis Macrocephalae Rhizoma.

In the present disclosure, the traditional Chinese herbal composition for the treatment of bacterial vaginosis may further preferably be prepared from the following components in parts by weight: 45 parts of the Zingiberis Rhizoma Recens, 40 parts of the Schisandrae *Chinensis* Fructus, 35 parts of the *Cinnamomi* Cortex, 35 parts of the Artemisiae *Argyi* Folium, 30 parts of the Codonopsis Radix, 30 parts of the compound traditional Chinese herbal fermentation broth, 25 parts of the Pulsatillae Radix, 23 parts of the Lonicerae Japonicae Flos, 18 parts of the *Taraxaci* Herba, 18 parts of Akebiae Caulis, 13 parts of the Polygoni Cuspidati Rhizoma et Radix, and 8 parts of the Atractylodis Macrocephalae Rhizoma.

In the present disclosure, the compound traditional Chinese herbal fermentation broth is specifically prepared by the following steps:

step 1, mixing the Sophorae Flavescentis Radix, the Artemisiae Annuae Herba, the Eucommiae Cortex, and the Coptidis Rhizoma, pulverizing and sieving to collect a sieved component;

step 2, mixing the sieved component with water and conducting a first decoction to obtain a decoction A and a decoction dreg A;

step 3, mixing the decoction dreg A with the water and conducting a second decoction to obtain a decoction B and a decoction dreg B;

step 4, mixing the decoction dreg B with the water and conducting a third decoction to obtain a decoction C and a decoction dreg C;

step 5, mixing the decoctions A, B and C, and conducting vacuum concentration to 1/6 to 1/4 of an original volume to obtain a compound traditional Chinese herbal decoction; and step 6, inoculating the *Lactobacillus acidophilus* into the compound traditional Chinese herbal decoction for a fermentation to obtain the compound traditional Chinese herbal fermentation broth.

In the specific preparation steps of the compound traditional Chinese herbal fermentation broth provided by the present disclosure, in step 1, the Sophorae Flavescentis Radix, the Artemisiae Annuae Herba, the Eucommiae Cortex, and the Coptidis Rhizoma may preferably be mixed in a mass ratio of (2-4):(1-3):(1-3):(1-2), and further preferably 3:2:2:1; a mesh number for the pulverizing and sieving may preferably be 150-250 mesh, further preferably 180-220 mesh, and still further preferably 200 mesh.

In the specific preparation steps of the compound traditional Chinese herbal fermentation broth provided by the present disclosure, in step 2, the sieved component may preferably be mixed with the water in a ratio of 1 g:(7-9) mL, and further preferably 1 g: 8 mL; the first decoction may preferably be conducted at a temperature of 90-100° C. for 45-55 min, further preferably at 92-98° C. for 48-52 min, and still further preferably at 95° C. for 50 min.

In the specific preparation steps of the compound traditional Chinese herbal fermentation broth provided by the present disclosure, in step 3, the decoction dreg A may preferably be mixed with the water in a ratio of 1 g:(4-6) mL, and further preferably 1 g: 5 mL; the second decoction may preferably be conducted at a temperature of 80-90° C. for 40-50 min, further preferably at 82-88° C. for 42-48 min, and still further preferably at 85° C. for 45 min.

In the specific preparation steps of the compound traditional Chinese herbal fermentation broth provided by the present disclosure, in step 4, the decoction dreg B may preferably be mixed with the water in a ratio of 1 g:(2-4) mL, and further preferably 1 g: 3 mL; the third decoction may preferably be conducted at a temperature of 70-80° C. for 30-40 min, further preferably at 72-78° C. for 32-38 min, and still further preferably at 75° C. for 35 min.

In the specific preparation steps of the compound traditional Chinese herbal fermentation broth provided by the present disclosure, in step 5, the decoctions A, B and C are mixed for conducting vacuum concentration to 1/6 to 1/4 of an original volume to obtain a compound traditional Chinese herbal decoction; further preferably, the decoctions A, B and C are mixed for conducting vacuum concentration to 1/5 of the original volume to obtain a compound traditional Chinese herbal decoction.

In the specific preparation steps of the compound traditional Chinese herbal fermentation broth provided by the present disclosure, in step 5, the vacuum concentration may preferably be conducted at a temperature of 35-45° C., further preferably at 38-42° C., and still further preferably at 40° C.

In the specific preparation steps of the compound traditional Chinese herbal fermentation broth provided by the present disclosure, in step 6, an inoculum size of the *Lactobacillus acidophilus* may preferably account for 4-6% of a volume of the compound traditional Chinese herbal decoction, and further preferably 5% of the volume of the compound traditional Chinese herbal decoction; the fermentation may preferably be conducted at a temperature of 35-40° C. for 25-45 h, further preferably at 36-38° C. for 30-40 h, and still further preferably at 37° C. for 35 h.

The present disclosure further provides a preparation method of the foregoing traditional Chinese herbal composition for the treatment of bacterial vaginosis, including the following steps:

step (1), mixing the Zingiberis Rhizoma Recens with the Schisandrae *Chinensis* Fructus, the *Cinnamomi* Cortex, the Artemisiae *Argyi* Folium, the Codonopsis Radix, the Pulsatillae Radix, the Lonicerae Japonicae Flos, the *Taraxaci* Herba, the Akebiae Caulis, the Polygoni Cuspidati Rhizoma et Radix and the Atractylodis Macrocephalae Rhizoma, pulverizing and sieving to collect a sieved component;

step (2), mixing the sieved component with the water for decoction to obtain a mixture; and step (3), conducting the vacuum concentration on the mixture to 1/6 to 1/4 of the original volume, and mixing the compound traditional Chinese herbal fermentation broth to obtain the traditional Chinese herbal composition for the treatment of bacterial vaginosis.

In the present disclosure, in step (1), a mesh number for the pulverizing and sieving may preferably be 150-250 mesh, further preferably 180-220 mesh, and still further preferably 200 mesh.

In the present disclosure, in step (2), the sieved component may preferably be mixed with the water in a ratio of 1 g: 4-6) mL, and further preferably 1 g: 5 mL; the first decoction may preferably be conducted at a temperature of 80-90° C. for 40-50 min, further preferably at 82-88° C. for 42-48 min, and still further preferably at 85° C. for 45 min.

In the present disclosure, in step (3), the vacuum concentration may preferably be conducted at a temperature of 35-45° C., further preferably at 38-42° C., and still further preferably at 40° C.

In the present disclosure, in step (3), the vacuum concentration is conducted on the mixture to 1/6 to 1/4 of the volume and mixed with the compound traditional Chinese herbal fermentation broth to obtain the traditional Chinese herbal composition for the treatment of bacterial vaginosis; further preferably, the vacuum concentration may be conducted on the mixture to 1/5 of the volume and mixed with the compound traditional Chinese herbal fermentation broth to obtain the traditional Chinese herbal composition for the treatment of bacterial vaginosis.

The technical solutions provided by the present disclosure will be described in detail below with reference to the examples, but they should not be construed as limiting the claimed scope of the present disclosure.

*Lactobacillus acidophilus* in the following examples were purchased from BeNa Culture Collection (BNCC)—Henan Engineering Research Center of Microbiological Culture Collection, with a deposit number of BNCC336636; *Lactobacillus bulgaricus* in the comparative examples were purchased from BNCC-Henan Engineering Research Center of Microbiological Culture Collection, with a deposit number of BNCC189751; the remaining raw materials are commercially available.

Example 1

I. Preparation of a Compound Traditional Chinese Herbal Fermentation Broth:

Step 1, Sophorae Flavescentis Radix, Artemisiae Annuae Herba, Eucommiae Cortex, and Coptidis Rhizoma were mixed in a mass ratio of 2:1:1:1, pulverized and sieved through a 150-mesh sieve to collect a sieved component;

Step 2, the sieved component was mixed with water in a ratio of 1 g: 7 mL and subjected to the first decoction at 90° C. for 45 min to obtain a decoction A and a decoction dreg A;

Step 3, the decoction dreg A was mixed with water in a ratio of 1 g: 4 mL and subjected to the second decoction at 80° C. for 40 min to obtain a decoction B and a decoction dreg B;

Step 4, the decoction dreg B was mixed with water in a ratio of 1 g: 2 mL and subjected to the third decoction at 70° C. for 30 min to obtain a decoction C and a decoction dreg C;

Step 5, the decoctions A, B and C were mixed and subjected to vacuum concentration to ¼ of the original volume at 35° C. to obtain a compound traditional Chinese herbal decoction; and Step 6, *Lactobacillus acidophilus* was inoculated into the compound traditional Chinese herbal decoction according to the inoculum size that accounted for 4% of the volume of the compound traditional Chinese herbal decoction and fermented at 35° C. for 25 h to obtain the compound traditional Chinese herbal fermentation broth.

II. Preparation of a Traditional Chinese Herbal Composition for the Treatment of Bacterial Vaginosis:

Step (1), 25 parts by weight of the foregoing compound traditional Chinese herbal fermentation broth, 40 parts by weight of Zingiberis Rhizoma Recens, 35 parts by weight of Schisandrae *Chinensis* Fructus, 30 parts by weight of *Cinnamomi* Cortex, 30 parts by weight of Artemisiae *Argyi* Folium, 25 parts by weight of Codonopsis Radix, 20 parts by weight of Pulsatillae Radix, 20 parts by weight of Lonicerae Japonicae Flos, 15 parts by weight of *Taraxaci* Herba, 15 parts by weight of Akebiae Caulis, 10 parts by weight of Polygoni Cuspidati Rhizoma et Radix, and 5 parts by weight of Atractylodis Macrocephalae Rhizoma were prepared;

Step (2), 40 parts by weight of Zingiberis Rhizoma Recens were mixed with 35 parts by weight of Schisandrae *Chinensis* Fructus, 30 parts by weight of *Cinnamomi* Cortex, 30 parts by weight of Artemisiae *Argyi* Folium, 25 parts by weight of Codonopsis Radix, 20 parts by weight of Pulsatillae Radix, 20 parts by weight of Lonicerae Japonicae Flos, 15 parts by weight of *Taraxaci* Herba, 15 parts by weight of Akebiae Caulis, 10 parts by weight of Polygoni Cuspidati Rhizoma et Radix, and 5 parts by weight of Atractylodis Macrocephalae Rhizoma, pulverized and sieved through a 150-mesh sieve to collect a sieved component;

Step (3), the sieved component was mixed with water in a ratio of 1 g: 4 mL and decocted at 80° C. for 40 min to obtain a mixture; and Step (4), the mixture was subjected to vacuum concentration to ¼ of the original volume at 35° C., and mixed with 25 parts by weight of the compound traditional Chinese herbal fermentation broth to obtain the traditional Chinese herbal composition for the treatment of bacterial vaginosis.

Example 2

I. Preparation of a Compound Traditional Chinese Herbal Fermentation Broth:

Step 1, Sophorae Flavescentis Radix, Artemisiae Annuae Herba, Eucommiae Cortex, and Coptidis Rhizoma were mixed in a mass ratio of 3:2:2:1, pulverized and sieved through a 200-mesh sieve to collect a sieved component;

Step 2, the sieved component was mixed with water in a ratio of 1 g: 8 mL and subjected to the first decoction at 95° C. for 50 min to obtain a decoction A and a decoction dreg A;

Step 3, the decoction dreg A was mixed with water in a ratio of 1 g: 5 mL and subjected to the second decoction at 85° C. for 45 min to obtain a decoction B and a decoction dreg B;

Step 4, the decoction dreg B was mixed with water in a ratio of 1 g: 3 mL and subjected to the third decoction at 75° C. for 35 min to obtain a decoction C and a decoction dreg C;

Step 5, the decoctions A, B and C were mixed and subjected to vacuum concentration to 1/5 of the original volume 40° C. to obtain a compound traditional Chinese herbal decoction; and Step 6, *Lactobacillus acidophilus* was inoculated into the compound traditional Chinese herbal decoction according to the inoculum size that accounted for 5% of the volume of the compound traditional Chinese herbal decoction and fermented at 37° C. for 35 h to obtain the compound traditional Chinese herbal fermentation broth.

II. Preparation of a Traditional Chinese Herbal Composition for the Treatment of Bacterial Vaginosis:

Step (1), 30 parts by weight of the foregoing compound traditional Chinese herbal fermentation broth, 45 parts by weight of Zingiberis Rhizoma Recens, 40 parts by weight of Schisandrae *Chinensis* Fructus, 35 parts by weight of *Cinnamomi* Cortex, 35 parts by weight of Artemisiae *Argyi* Folium, 30 parts by weight of Codonopsis Radix, 25 parts by weight of Pulsatillae Radix, 23 parts by weight of Lonicerae Japonicae Flos, 18 parts by weight of *Taraxaci* Herba, 18 parts by weight of Akebiae Caulis, 13 parts by weight of Polygoni Cuspidati Rhizoma et Radix, and 8 parts by weight of Atractylodis Macrocephalae Rhizoma were prepared;

Step (2), 45 parts by weight of Zingiberis Rhizoma Recens were mixed with 40 parts by weight of Schisandrae *Chinensis* Fructus, 35 parts by weight of *Cinnamomi* Cortex, 35 parts by weight of Artemisiae *Argyi* Folium, 30 parts by weight of Codonopsis Radix, 25 parts by weight of Pulsatillae Radix, 23 parts by weight of Lonicerae Japonicae Flos, 18 parts by weight of *Taraxaci* Herba, 18 parts by weight of Akebiae Caulis, 13 parts by weight of Polygoni Cuspidati Rhizoma et Radix, and 8 parts by weight of Atractylodis Macrocephalae Rhizoma, pulverized and sieved through a 200-mesh sieve to collect a sieved component;

Step (3), the sieved component was mixed with water in a ratio of 1 g: 5 mL and decocted at 85° C. for 45 min to obtain a mixture; and Step (4), the mixture was subjected to vacuum concentration to 1/5 of the original volume at 40° C., and mixed with 30 parts by weight of the compound traditional Chinese herbal fermentation broth to obtain the traditional Chinese herbal composition for the treatment of bacterial vaginosis.

Example 3

I. Preparation of a Compound Traditional Chinese Herbal Fermentation Broth:

Step 1, Sophorae Flavescentis Radix, Artemisiae Annuae Herba, Eucommiae Cortex, and Coptidis Rhizoma were mixed in a mass ratio of 4:3:3:2, pulverized and sieved through a 250-mesh sieve to collect a sieved component;

Step 2, the sieved component was mixed with water in a ratio of 1 g: 9 mL and subjected to the first decoction at 100° C. for 55 min to obtain a decoction A and a decoction dreg A;

Step 3, the decoction dreg A was mixed with water in a ratio of 1 g: 6 mL and subjected to the second decoction at 90° C. for 50 min to obtain a decoction B and a decoction dreg B;

Step 4, the decoction dreg B was mixed with water in a ratio of 1 g: 4 mL and subjected to the third decoction at 80° C. for 40 min to obtain a decoction C and a decoction dreg C;

Step 5, the decoctions A, B and C were mixed and subjected to vacuum concentration to 1/6 of the original volume 45° C. to obtain a compound traditional Chinese herbal decoction; and Step 6, *Lactobacillus acidophilus* was inoculated into the compound traditional Chinese herbal decoction according to the inoculum size that accounted for 6% of the volume of the compound traditional Chinese herbal decoction and fermented at 40° C. for 45 h to obtain the compound traditional Chinese herbal fermentation broth.

II. Preparation of a Traditional Chinese Herbal Composition for the Treatment of Bacterial Vaginosis:

Step (1), 35 parts by weight of the foregoing compound traditional Chinese herbal fermentation broth, 50 parts by weight of Zingiberis Rhizoma Recens, 45 parts by weight of Schisandrae *Chinensis* Fructus, 40 parts by weight of *Cinnamomi* Cortex, 40 parts by weight of Artemisiae *Argyi* Folium, 35 parts by weight of Codonopsis Radix, 30 parts by weight of Pulsatillae Radix, 25 parts by weight of Lonicerae Japonicae Flos, 20 parts by weight of *Taraxaci* Herba, 20 parts by weight of Akebiae Caulis, 15 parts by weight of Polygoni Cuspidati Rhizoma et Radix, and 10 parts by weight of Atractylodis Macrocephalae Rhizoma were prepared;

Step (2), 50 parts by weight of Zingiberis Rhizoma Recens were mixed with 45 parts by weight of Schisandrae *Chinensis* Fructus, 40 parts by weight of *Cinnamomi* Cortex, 40 parts by weight of Artemisiae *Argyi* Folium, 35 parts by weight of Codonopsis Radix, 30 parts by weight of Pulsatillae Radix, 25 parts by weight of Lonicerae Japonicae Flos, 20 parts by weight of *Taraxaci* Herba, 20 parts by weight of Akebiae Caulis, 15 parts by weight of Polygoni Cuspidati Rhizoma et Radix, and 10 parts by weight of Atractylodis Macrocephalae Rhizoma, pulverized and sieved through a 250-mesh sieve to collect a sieved component;

Step (3), the sieved component was mixed with water in a ratio of 1 g: 6 mL and decocted at 90° C. for 50 min to obtain a mixture; and Step (4), the mixture was subjected to vacuum concentration to 1/6 of the original volume at 45° C., and mixed with 35 parts by weight of the compound traditional Chinese herbal fermentation broth to obtain the traditional Chinese herbal composition for the treatment of bacterial vaginosis.

Comparative Example 1

Except for omitting the step of fermenting the compound traditional Chinese herbal decoction with *Lactobacillus acidophilus* in step 6, all other steps and step parameters remained the same as those in Example 2.

Comparative Example 2

Except that Step 6 was changed, namely, "*Lactobacillus bulgaricus* was inoculated into the compound traditional Chinese herbal decoction according to the inoculum size that accounted for 5% of the volume of the compound traditional Chinese herbal decoction and fermented at 42° C. for 35 h to obtain the compound traditional Chinese herbal fermentation broth", all other steps and step parameters remained the same as those in Example 2.

Comparative Example 3

Except for changing "Sophorae Flavescentis Radix, Artemisiae Annuae Herba, Eucommiae Cortex, and Coptidis Rhizoma" in step 1) to "Scutellariae Radix, Pogostemonis Herba, Stemonae Radix, and Phellodendri *Chinensis* Cortex", all other steps and step parameters remained the same as those in Example 2.

Comparative Example 4

Except for omitting the Zingiberis Rhizoma Recens component, all other steps and step parameters remained the same as those in Example 2.

Comparative Example 5

Except for omitting the preparation and addition of the compound traditional Chinese herbal fermentation broth, all other steps and step parameters remained the same as those in Example 2.

Experimental Example 1

Taking Example 2 and Comparative Examples 1-5 as examples, different traditional Chinese herbal compositions were diluted with 15 times the volume of water to detect the inhibitory effects of diluents of different Chinese herbal compositions on *Gardnerella vaginalis* (GV) (purchased from Ningbo Testobio Co., Ltd., Cat #TS275631), *Peptostreptococcus* sp. (purchased from Ningbo Testobio Co., Ltd., Cat #TS321157), and *Bacteroides* vulgatus (purchased from Ningbo Testobio Co., Ltd., Cat #TS307466). The results are shown in Table 1.

TABLE 1

| | The inhibition rate (%) of diluents of different Chinese herbal compositions | | |
|---|---|---|---|
| Group | *Gardnerella vaginalis* (GV) | *Peptostreptococcus* sp. | *Bacteroides vulgatus* |
| Example 2 | 99.5 | 98.6 | 99.2 |
| Comparative Example 1 | 59.7 | 54.3 | 61.2 |
| Comparative Example 2 | 70.6 | 65.6 | 69.8 |
| Comparative Example 3 | 52.4 | 51.7 | 58.2 |
| Comparative Example 4 | 49.8 | 50.6 | 51.3 |
| Comparative Example 5 | 45.6 | 43.2 | 30.5 |

From Table 1, it can be seen that compared with Comparative Examples 1 to 5, the traditional Chinese herbal composition in Example 2 of the present disclosure has better inhibitory effects on *Gardnerella vaginalis* (GV), *Peptostreptococcus* sp. and *Bacteroides* vulgatus, and the inhibition rate of each pathogenic bacteria is as high as more than 98%. Compared with Comparative Example 1, in which *Lactobacillus acidophilus* was not used for fermentation, fermentation with this strain in Example 2 of the present disclosure is more conducive to inhibiting vaginal pathogenic bacteria. This indicates that the fermentation of Sophorae Flavescentis Radix, Artemisiae Annuae Herba, Eucommiae Cortex and Coptidis Rhizoma with *Lactobacillus acidophilus* can substantially enhance its antimicrobial function.

Example 2

Taking Example 2 and Comparative Examples 2 and 3 as examples, MRS Agar (peptone 10.0 g, beef extract 10.0 g, yeast powder 4.0 g, glucose 20.0 g, magnesium sulfate 0.2 g, sodium acetate 5.0 g, triammonium citrate 2.0 g, dipotassium hydrogen phosphate 2.0 g, manganese sulfate 0.04 g, Tween 80 1.0 g, and distilled water 1.0 L. pH 5.7. Sterilization at 121° C. for 15 min) and MRS Agar (peptone 10.0 g, beef extract powder 8.0 g, yeast powder 4.0 g, glucose 20.0 g, magnesium sulfate 0.2 g, sodium acetate 5.0 g, diammonium citrate 2.0 g, dipotassium hydrogen phosphate 2.0 g, manganese sulfate 0.04 g, Tween 80 1.0 g, and distilled water 1.0 L. pH 5.7. Sterilization at 118° C. for 15 min) were used as blank controls 1 and 2, respectively. Herein, the culture and inoculum size of the blank control 1 were consistent with those in Example 2 and Comparative Example 3, and the blank control 1 was cultured at 37° C. for 35 h under anaerobic conditions; the culture and inoculum size of the blank control 2 were consistent with those in Comparative Example 2, and the blank control 2 was cultured at 42° C. for 35 h under anaerobic conditions. The viable count of lactic acid bacteria in the compound traditional Chinese herbal fermentation broths of Example 2 and Comparative Examples 2 and 3 and that of cultured lactic acid bacteria of blank controls 1 and 2 were detected. The results are shown in Table 2.

TABLE 2

The viable count of lactic acid bacteria after different treatment

| Group | Viable count (CFU/mL) |
|---|---|
| Example 2 | $4.43 \times 10^{10}$ |
| Comparative Example 2 | $3.51 \times 10^{8}$ |
| Comparative Example 3 | $3.26 \times 10^{7}$ |
| Blank control 1 | $2.28 \times 10^{8}$ |
| Blank control 2 | $3.25 \times 10^{8}$ |

From Table 2, compared with the blank control 1, Example 2 of the present disclosure can significantly increase the viable count of *Lactobacillus acidophilus*, while Comparative Example 3 significantly reduces it. This indicates that not all traditional Chinese herbal fermentations can increase the viable count of lactic acid bacteria. Only the traditional Chinese herbal fermentation in the present disclosure can promote the multiplication of *Lactobacillus acidophilus*. Compared with blank control 2, Comparative Example 2 can increase the viable count of *Lactobacillus bulgaricus*, but the increase and final viable count are much smaller than those of Example 2 of the present disclosure. This shows that the fermentation strain will also affect the final fermentation effect. Only the fermentation of the Chinese medicinal materials of the present disclosure with *Lactobacillus acidophilus* can substantially increase the viable count of lactic acid bacteria.

Experimental Example 3

Taking the traditional Chinese herbal compositions in Example 2 and Comparative Examples 1 to 5 as examples, therapeutic effects of different products on patients with bacterial vaginosis were investigated using commercially available Jieeryin and Fuyanjie as control groups: in June 2022, 80 patients (aged 35-45 years) diagnosed with bacterial vaginosis were randomly divided into 8 groups of 10 patients, who used the traditional Chinese herbal compositions in Example 2 and Comparative Examples 1 to 5 of the present disclosure, Jieeryin, and Fuyanjie respectively. The application method was as follows: the traditional Chinese herbal compositions prepared in Example 2 and Comparative Examples 1 to 5 were mixed with 60° C. warm water in a volume ratio of 1:15, respectively, and the vagina was irrigated once a day. Jieeryin and Fuyanjie were used according to the instructions. A course of treatment lasted for 7 days. After two courses of treatment, vaginal secretions were reviewed. If the patient slowly improves during the treatment, the vaginal secretions should be tested normal after two courses of treatment, without signs of vaginitis. Moreover, if there is no recurrence after a 3-month follow-up, it should be indicate that the patient recovers. The statistical results after follow-up are shown in Table 3.

TABLE 3

Therapeutic effects of different products on patients with bacterial vaginosis

| Group | Number of recovered patients |
|---|---|
| Example 2 | 10 |
| Comparative Example 1 | 4 |
| Comparative Example 2 | 6 |
| Comparative Example 3 | 4 |
| Comparative Example 4 | 3 |
| Comparative Example 5 | 2 |
| Jieeryin | 4 |
| Fuyanjie | 5 |

From Table 3, compared with Comparative Examples 1 to 5, the Jieeryin group and the Fuyanjie group, the recovery rate can be up to 100% after using the traditional Chinese herbal composition in Example 2 of the present disclosure. It is indicated that the traditional Chinese herbal composition provided by the present disclosure has a significant beneficial effect on the treatment of bacterial vaginosis, which can substantially improve the quality of life of patients.

The above descriptions are merely preferred implementations of the present disclosure. It should be noted that a person of ordinary skill in the art may further make several improvements and modifications without departing from the principle of the present disclosure, but such improvements and modifications should be deemed as falling within the claimed scope of the present disclosure.

What is claimed is:

1. A traditional Chinese herbal composition for the treatment of bacterial vaginosis, comprising the following components in parts by weight: 40-50 parts of Zingiberis Rhizoma Recens, 35-45 parts of Schisandrae *Chinensis* Fructus, 30-40 parts of *Cinnamomi* Cortex, 30-40 parts of Artemisiae *Argyi* Folium, 25-35 parts of Codonopsis Radix, 25-35 parts of a compound traditional Chinese herbal fermentation broth, 20-30 parts of Pulsatillae Radix, 20-25 parts of Lonicerae Japonicae Flos, 15-20 parts of *Taraxaci* Herba, 15-20 parts of Akebiae Caulis, 10-15 parts of Polygoni Cuspidati Rhizoma et Radix, and 5-10 parts of Atractylodis Macrocephalae Rhizoma, wherein the compound traditional Chinese herbal fermentation broth is obtained by fermenting Sophorae Flavescentis Radix, Artemisiae Annuae Herba, Eucommiae Cortex, and Coptidis Rhizoma with *Lactobacillus acidophilus*.

2. The traditional Chinese herbal composition for the treatment of bacterial vaginosis according to claim 1, wherein the compound traditional Chinese herbal fermentation broth is specifically prepared by the following steps:
   step 1, mixing the Sophorae Flavescentis Radix, the Artemisia Annuae Herba, the Eucommiae Cortex, and the Coptidis Rhizoma, pulverizing and sieving to collect a sieved component;
   step 2, mixing the sieved component with water and conducting a first decoction to obtain a decoction A and a decoction dreg A;
   step 3, mixing the decoction dreg A with the water and conducting a second decoction to obtain a decoction B and a decoction dreg B;
   step 4, mixing the decoction dreg B with the water and conducting a third decoction to obtain a decoction C and a decoction dreg C;
   step 5, mixing the decoctions A, B and C, and conducting vacuum concentration to 1/6 to 1/4 of an original volume to obtain a compound traditional Chinese herbal decoction; and
   step 6, inoculating the *Lactobacillus acidophilus* into the compound traditional Chinese herbal decoction for a fermentation to obtain the compound traditional Chinese herbal fermentation broth.

3. The traditional Chinese herbal composition for the treatment of bacterial vaginosis according to claim 2, wherein in step 1, the Sophorae Flavescentis Radix, the Artemisiae Annuae Herba, the Eucommiae Cortex, and the Coptidis Rhizoma are mixed in a mass ratio of (2-4):(1-3):(1-3):(1-2), and a mesh number for the pulverizing and sieving is 150-250 mesh.

4. The traditional Chinese herbal composition for the treatment of bacterial vaginosis according to claim 2, wherein in step 2, the sieved component is mixed with the water in a ratio of 1 g:(7-9) mL; the first decoction is conducted at a temperature of 90-100° C. for 45-55 min;
   in step 3, the decoction dreg A is mixed with the water in a ratio of 1 g:(4-6) mL; the second decoction is conducted at a temperature of 80-90° C. for 40-50 min; and
   in step 4, the decoction dreg B is mixed with the water in a ratio of 1 g:(2-4) mL; the third decoction is conducted at a temperature of 70-80° C. for 30-40 min.

5. The traditional Chinese herbal composition for the treatment of bacterial vaginosis according to claim 2, wherein in step 5, the vacuum concentration is conducted at a temperature of 35-45° C.

6. The traditional Chinese herbal composition for the treatment of bacterial vaginosis according to claim 2, wherein in step 6, an inoculum size of the *Lactobacillus acidophilus* accounts for 4-6% of a volume of the compound traditional Chinese herbal decoction, and the fermentation is conducted at a temperature of 35-40° C. for 25-45 h.

7. A preparation method of the traditional Chinese herbal composition for the treatment of bacterial vaginosis according to claim 1, comprising the following steps:
   step (1), mixing the Zingiberis Rhizoma Recens with the Schisandrae *Chinensis* Fructus, the *Cinnamomi* Cortex, the Artemisiae *Argyi* Folium, the Codonopsis Radix, the Pulsatillae Radix, the Lonicerae Japonicae Flos, the *Taraxaci* Herba, the Akebiae Caulis, the Polygoni Cuspidati Rhizoma et Radix and the Atractylodis Macrocephalae Rhizoma, pulverizing and sieving to collect a sieved component;
   step (2), mixing the sieved component with the water for decoction to obtain a mixture; and
   step (3), conducting the vacuum concentration on the mixture to 1/6 to 1/4 of the original volume, and mixing the compound traditional Chinese herbal fermentation broth to obtain the traditional Chinese herbal composition for the treatment of bacterial vaginosis.

8. The preparation method of the traditional Chinese herbal composition for the treatment of bacterial vaginosis according to claim 7, wherein in step (1), a mesh number for the pulverizing and sieving is 150-250 mesh.

9. The preparation method of the traditional Chinese herbal composition for the treatment of bacterial vaginosis according to claim 7, wherein in step (2), the sieved component is mixed with the water in a ratio of 1 g:(4-6) mL, and the decoction is conducted at a temperature of 80-90° C. for 40-50 min.

10. The preparation method of the traditional Chinese herbal composition for the treatment of bacterial vaginosis according to claim 7, wherein in step (3), the vacuum concentration is conducted at a temperature of 35-45° C.

\* \* \* \* \*